United States Patent [19]

Renevot

[11] 4,154,664

[45] May 15, 1979

[54] PROBE FOR MEASURING GASEOUS COMPONENTS

[75] Inventor: Gerard Renevot, Paris, France

[73] Assignee: Regie Natinale des Usines Renault, Boulogne Billancourt, France

[21] Appl. No.: 788,350

[22] Filed: Apr. 18, 1977

[30] Foreign Application Priority Data

Apr. 16, 1977 [FR] France .................................. 76 11329
Feb. 18, 1977 [FR] France .................................. 77 04846

[51] Int. Cl.² ............................................. G01N 27/46
[52] U.S. Cl. ................................... 204/195 S; 204/1 T
[58] Field of Search ............................. 204/1 S, 195 S

[56] References Cited

U.S. PATENT DOCUMENTS

| | | | |
|---|---|---|---|
| B 843,038 | 2/1976 | Sandler | 204/195 S |
| 3,309,233 | 3/1967 | McPheeters et al. | 204/195 S |
| 3,347,767 | 10/1967 | Hickam | 204/195 S |
| 3,630,874 | 12/1971 | Olette et al. | 204/195 S |
| 3,844,920 | 10/1974 | Burgett et al. | 204/195 S |
| 3,847,778 | 11/1974 | Riddel | 204/195 S |
| 3,857,760 | 12/1974 | Breuer et al. | 204/195 S |
| 3,891,529 | 6/1975 | Beesch | 204/195 S |
| 3,960,693 | 6/1976 | Weyl et al. | 204/195 S |

*Primary Examiner*—T. Tung
*Attorney, Agent, or Firm*—Oblon, Fisher, Spivak, McClelland & Maier

[57] ABSTRACT

A probe for detecting variations in the composition of a mixed-gas flow, designed primarily for monitoring variations in the composition of exhaust gases of an internal combustion engine for anti-pollution purposes and based on the pile effect in a solid electrolyte, one side of which is exposed to the gas being tested and the other to a reference gas, the solid electrolyte having the form of a tube open at its ends and traversed by the reference gas passing through its interior, while its outer surface is in contact with the gas flow under test. The electrolyte tube is inserted transversely into the flow passage, its reference gas being released into the passage through the orifice in the free end of the tube.

20 Claims, 10 Drawing Figures

PROBE FOR MEASURING GASEOUS COMPONENTS

BACKGROUND OF THE INVENTION

1. Field of the Invention:

The present invention relates to a probe for detecting variations in the composition of a flow of mixed gases and in particular of the exhaust gases of clean-burning internal combustion engines.

2. Description of the Prior Art:

Known probes, called "lambda probes", for detecting variations in the composition of exhaust gases, usually consist of a solid-electrolyte partition, e.g. of zirconium oxide, producing a potential difference between one side which is subjected to the exhaust gases and the other side which is exposed to the atmosphere. These partitions generally have a closed tubular form called "glove-finger", or are flat plates. These types have drawbacks.

For the "glove-finger" probe, the reference zone being a relatively closed volume of air within the "finger", the renewal of this air is poor and there accordingly is a risk of its being polluted by the surrounding exhaust gases, especially if the sealing between the air and exhaust-gas zones is not perfect. The normally occuring expansions and vibrations make this sealing difficult, particularly for the flat plate or lozenge configuration, where the seal must necessarily be exposed to the high-temperature exhaust-gas flow.

These two aspects of existing embodiments thus call for a complicated technology entailing delicate and therefore difficult fabrication, the more so because the severe operating conditions often require their replacement because of rupture or fouling.

The replacement of these probes is made difficult because of this complex technology and their operating environment, leading to oxidation and jamming of the assembled parts.

SUMMARY OF THE INVENTION

The object of the present invention is to provide an improved probe for detecting variations in the composition of exhaust gases, consisting essentially of a tube of solid electrolyte open at both ends and mounted transversely in the exhaust pipe. At least one end of the tube is in communication with the atmosphere, and this feature permits free circulation of the air within the tube.

According to this invention, the tube is supported by at least one seal installed exterior to the exhaust pipe in one of the coolest zones. The electrical connections are also mounted in these cool zones, one connection being at one end of the tube and the other connection being at the other end of the tube by the intermediary of a feedthrough in the outer portion of one of the supports of the seals.

The tube of solid electrolyte is protected externally by a perforated refractory steel tube.

More generally, the probe of the present invention has as its object the detection of variations in the composition of a flow of mixed gases based on the pile effect on a solid electrolyte, one side of which is subjected to the gases being tested and the other side of which is exposed to a reference gas. It is characterized by the fact that the solid electrolyte is in the form of a tube, open at its ends and surrounded by the flow of gas being tested, the reference gas passing through the interior of the tube. The flow of tested gases is through a pipe, the walls of which receive at least one tubular body, in which is compressed the seal providing centering for, and holding in position, the electrolyte tube passing through the seal. Compression of the seals is provided by threaded plugs having central holes in which the ends of the electrolyte tube fit freely and without contact. The electrolyte tube is enclosed, without contact, in the zone of flow of the gas tested by a protective tube, having perforations therein which allow passage of the gas around the outer surface of the electrolyte tube. The perforations consist of at least one longitudinal slot situated centrally on the frontal zone of the tube, receiving the flow of test gas, and lateral outlet holes for the flow collected by the frontal slot.

In another configuration, the perforations may be two lines of holes diametrically opposed in the direction of flow of the test gas.

The seals are advantageously made in the form of a copper-graphite sleeve compressed between two packing rings of refractory metal alloy wool making electrical contact with the outer surface of the electrolyte tube.

In another embodiment, the tubular bodies are lengthened to assure coooling of their ends against the heat of the test-gas flow, the ends receiving seals of plastic material, e.g. simple O-ring seals. The end seals may also compress a longitudinal seal of thermo-expandable material filling the space between the seal-holding tube and the electrolyte tube. The connecting wire to the reference electrode, in contact with the inner surface of the electrolyte tube, enters through the central hole for the reference gas in an insulating plug. Electrical contact of the connecting wire with the inner surface of the tube is assured by compression of a spring-metal extension of the wire forced into the tube.

In a principal application of the invention, the flow of test gas is the exhaust gas of an internal combustion engine in the exhaust pipe of the engine and is used for anti-pollution purposes. In this probe configuration of the invention, where the solid electrolyte is a tube open at both ends, the two ends of the probe are open to the atmosphere, thus permitting free circulation of air through the reference portion of the probe. Because of the constant renewal of the reference air, at least by convection due to heat exchange, perfect sealing of the assembly, indispensable for the glove-finger or lozenge probes, is not so imperative. The seals are moved back to the cooler regions, away from the flow of the exhaust gases, together with the electrical contacts, to the ends of the electrolyte tube. The solid electrolyte is protected inside the probe, for example, by a perforated tube of refractory steel providing protection against erosion and inhomogeneity of the gas at the catalytic coating. Removal and periodic replacement of the zirconia tube is made possible and, by reason of its tubular form, simple, this form permitting its fixation by just the seals into which it is slipped, and fabrication of the tube is simple and inexpensive, e.g., by extrusion, without the necessity of supplementary machining, nor any change in section or thickness, which also enhances its resistance to thermal shocks. The metal sleeves fastened to the exhaust pipe serve to provide a gastight seal,
electrical contacts,
assist in positioning of the zirconia tube,
help in damping of vibrations,
afford free expansion of the zirconia tube, and afford free expansion of the tube protecting the zirconia tube.

In a preferred embodiment the tube is fastened at only one point on the exhaust pipe. One open end of the solid electrolyte tube is put in contact with the gases to be tested inside the exhaust pipe, the other open end being outside the exhaust pipe, with the possibility of circulating a reference gas, e.g. air, through the inside of the solid electrolyte tube.

This probe, consisting essentially of an ion-conducting tube of solid electrolyte, open at its ends, is placed transversely in the exhaust pipe, the outer surface of the tube in contact with the exhaust gases being covered with a conducting and catalytic metallic layer.

This porous catalytic layer provides, in addition to its catalytic effect on the reaction with the elements being measured, the electrical connection to ground.

The inner surface of the solid electrolyte tube is likewise coated with a porous catalytic metallic deposit, not necessarily an electrical conductor, and is connected to a terminal insulated from ground. By the intermediary of this terminal, it is possible to effect a pneumatic connection for admitting a reference gas to the interior of the solid electrolyte, the reference gas chosen being air, for example.

By the intermediary of a source of air under pressure located outside the detector, the reference gas or "air", circulates through the interior of the solid electrolyte tube at a rate of flow regulated so as not to cool the inner surface of the zirconia tube significantly. This air flow is negligible in comparison with the total flow of exhaust gases and it does not disturb the oxygen content of the exhaust gases at the external catalytic layer because of the special design of the layer and the arrangement of the electrolyte tube in a metallic sleeve with multiple openings, the free end of the tube being even with a corresponding hole in the end of the sleeve.

The classical function of an electrochemical cell with an electrolytic force given by the law of NERNST is accordingly attained, the cell consisting of a partition, of zirconia for example, one side of which is the catalytic test electrode in contact with the gas being measured, and the other side of which is the reference electrode, catalytic or not, in contact with the reference gas, e.g. air.

BRIEF DESCRIPTION OF THE DRAWINGS

Various other objects, features and attendant advantages of the present invention will be more fully appreciated as the same becomes better understood from the following detailed description when considered in connection with the accompanying drawings, in which like reference characters designate like or corresponding parts throughout the several figures, and wherein.

DETAILED DESCRIPTION OF THE PREFERRED EMBODIMENT

Figure 1:
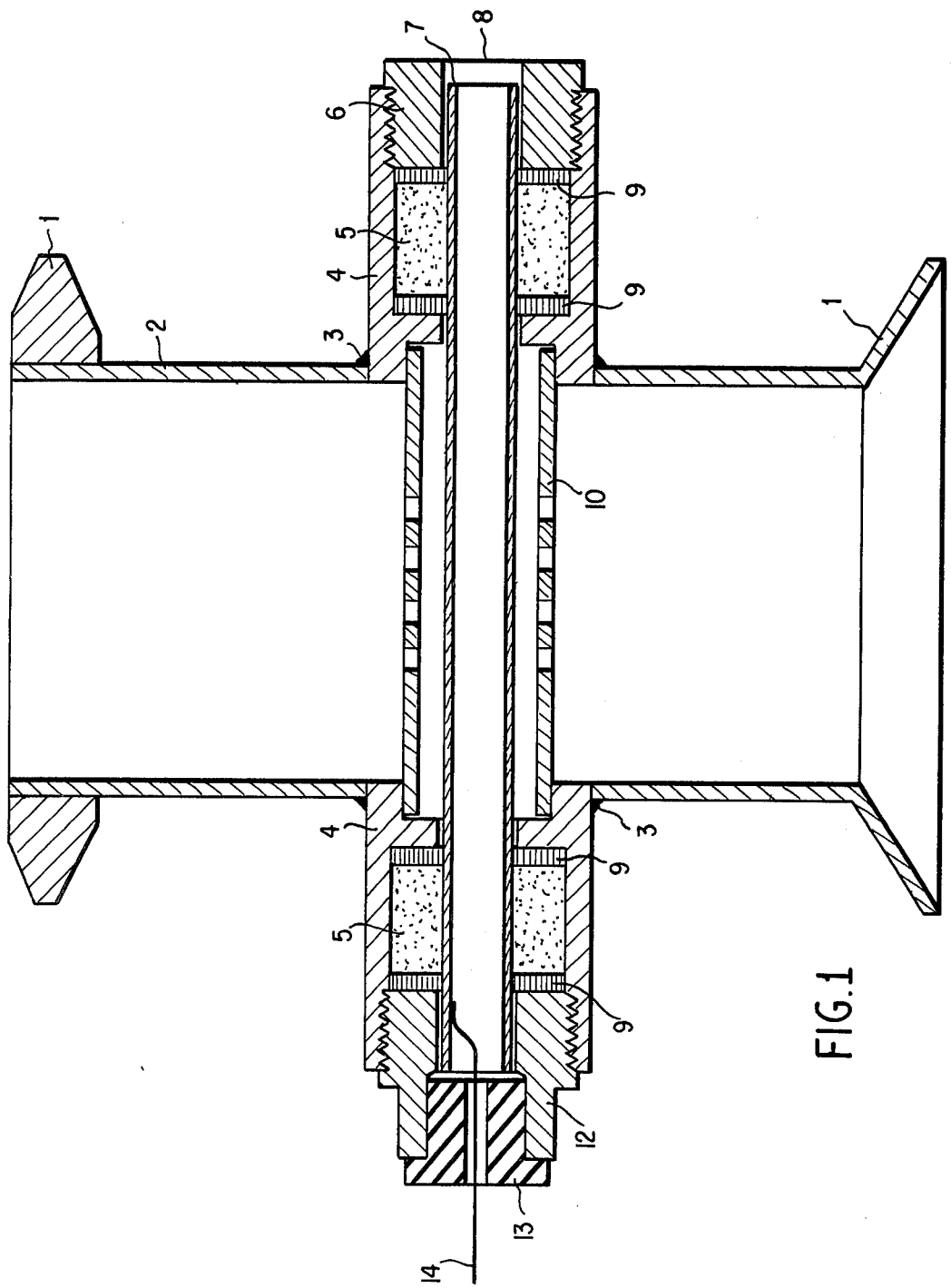
FIG. 1 shows, on an enlarged scale, a cross section of an exhaust pipe element equipped with the probe of the present invention.

Referring now to the drawings, and more particularly to FIG. 1, there is seen a piece of an exhaust pipe or conduit 2 which goes between the exhaust manifold and the pipe to the muffler, using attachment flanges 1. Tubular bodies 4, diametrically opposed, on the same diametric axis, are attached by welds 3 to the pipe 2. Seals 5, compressed inside the bodies 4 by screwing in the plugs 6, hold an electrolyte tube 7 of the probe, e.g., a ceramic one of stabilized fitted zirconia, on a diametric axis of the pipe 2.

On the face 8 of the plug 6, there can be provided a screen, e.g. a cover of elastic material, protecting the tube 7 from outside dust while still allowing gases to pass through. Similar protection can be assured at the other end by a plug 13, likewise of insulating plastic, inserted in the threaded plug 12, compressing the seal 5 on this end. A hole through the center of the plug 13 brings out the connecting wire 14 making contact with the inner coating of the zirconia tube 7.

Washers 9, e.g. of stainless or refractory steel wool or felt, are placed at both ends of the seals 5 to hold them laterally. On the other hand at the ends of a copper-graphite seal 5, there are provided two preformed pliable seals 9 of stainless steel wool.

A perforated tube 10 of stainless steel surrounds the electrolyte tube 7 of the probe where it passes through the exhaust pipe 2 to protect it from erosion by the exhaust gas flow.

Figure 2:
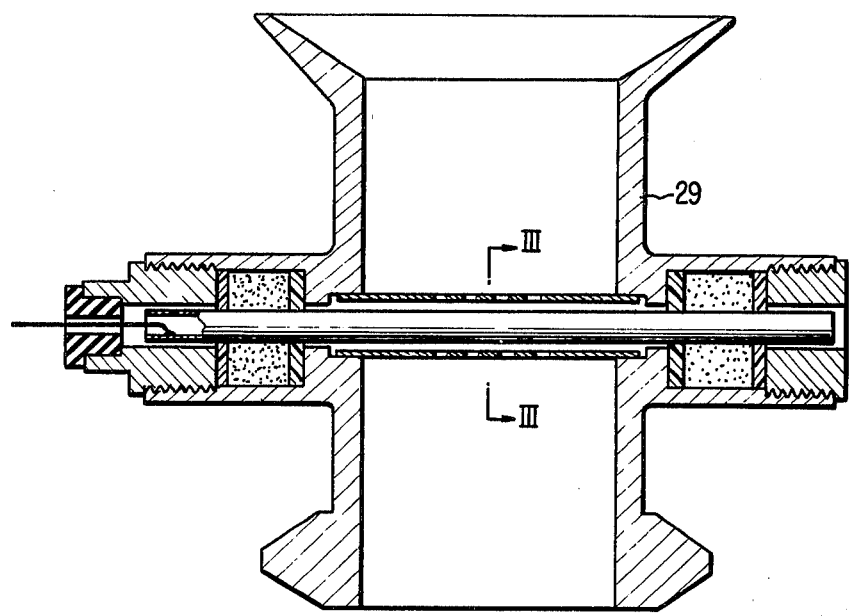
FIG. 2 shows, on a more reduced scale, the same element in the form of a casting.

In the variant of FIG. 2, where the element of exhaust pipe 1, 2 is made in the form of a casting 29, e.g., of refractory cast-iron, the tube 10 may be installed as an insert during the casting of the piece 29. The embodiment of FIG. 1 is made gastight by compression of copper-graphite seals 5 between the outside of the zirconia tube 7 and the insides of the sleeves 4, the role of which is to maintain the copper-graphite seals 5 in uniform compression. Compression of the seals 5 and 9 is thus obtained by screwing in the metal plugs 6 and 12. Any play between the outside of the zirconia tube 7 and the smallest inner diameter of the sleeve 4 will be of the order of 0.1 to 2 mm, and preferably 0.5 to 0.8 mm.

The embodiment of FIG. 2 shows the same method of sealing as set forth in FIG. 1.

Figure 5:
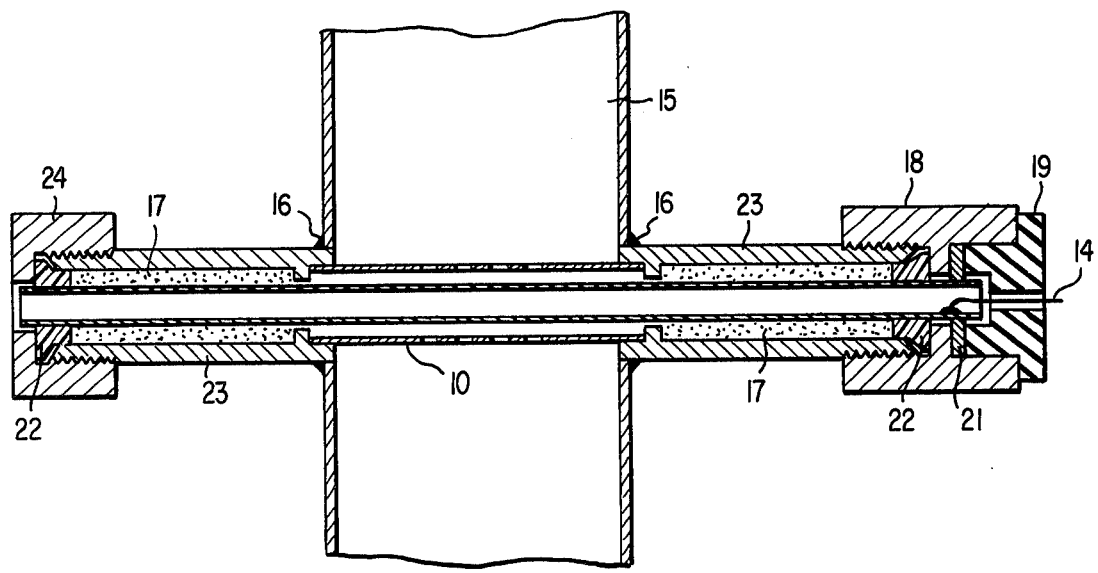
FIG. 5 shows an embodiment of the mounting seal using thermoexpandable material.
Figure 6:
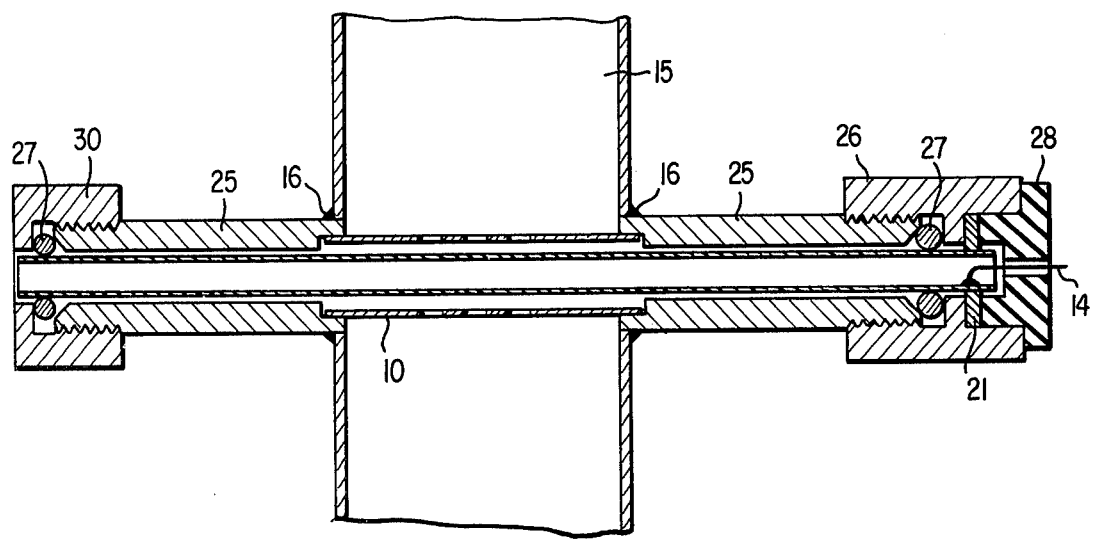
FIG. 6 is another embodiment of the seals, using simple toroidal seals.

In the embodiments of FIGS. 5 and 6, the sealing is effected at a lower temperature at the ends of the sleeves 23 and 25 by O-ring seals 27, or seals 22 of appropriate shape, placed under compression by the plugs 18 and 24, or 26 and 30. The seals 22 and 27 may be of plastic material, such as Teflon or Viton. Their permissible operating temperature will not be exceeded if the length of the sleeve 23 or 25 is made great enough to permit sufficient cooling of their ends.

According to FIG. 5 the space 17 in the sleeve may be filled with thermo-expandable material which further ensures better positioning of the zirconia tube. Such thermo-expandable materials are commercially available, notably one sold by the 3M Co. (Minnesota Mining and Manufacturing Co.) which doubles in volume at 650° C. and is suited to such applications. The play between the outside of the zirconia tube 7 and the smallest diameter of the sleeves 18, 23 or 25 will be:

0.1 to 2 mm and preferably 0.5 to 0.8 mm for the case of FIG. 5 and 0.1 to 2 mm and preferably 1 mm for the case of FIG. 6.

The advantageous solid electrolyte for tube 7 is zirconium oxide, stablized with lime or yttrium oxide. The tube 7 is open at both ends and may be between 4 and 12 mm, preferably 6 mm, in outer diameter and between 2 and 10 mm, and preferably 4 mm, in inner diameter.

The inner and outer surfaces of the tube will be coated with a catalytic metallic deposit applied by evaporation under vacuum by known techniques.

Figure 3A:
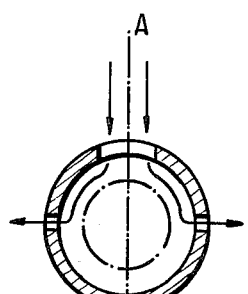
FIG. 3a is a transverse sectional view, along the line III FIG. 2.
Figure 3B:
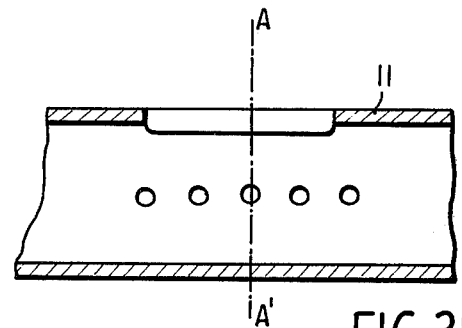
FIG. 3b is a longitudinal section of an example of the protective tube of the probe showing the openings permitting easy flow and renewal of the exhaust gases around the electrolyte tube of the probe.
Figure 4A:
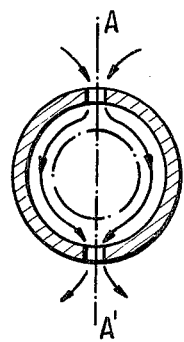
FIGS. 4a and 4b show similar views of another arrangement of flow holes.
Figure 4B:
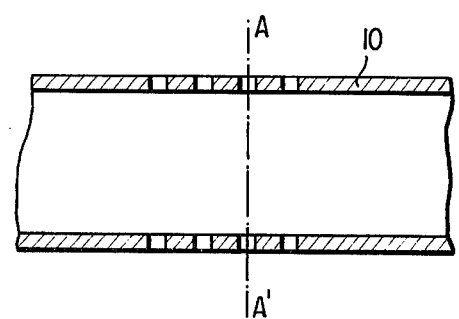

The zirconia tube 7 is protected by the concentric outer metallic tube 10 or 11. FIGS. 3a and 3b show an example of perforations consisting of two parallel frontal slots facing into the flow of the exhaust gases (direction of the arrows at A in FIG. 2a) which escape by the lateral holes after turbulent mixing in the space between the two tubes. FIGS. 4a and 4b show another example of realizing the perforations, namely two rows of holes being located diametrically opposed in the direction of flow.

One can envisage the possibility for the refractory steel tube to expand freely in the two seats in the sleeves 4.

In this case, the play between the outside of the tube and the inner diameter of the sleeve 4 will be from 0.1 to 0.3 mm and preferably 0.1 to 0.2 mm, while the play between the end of the tube 10 and the bottom of the seat in the sleeve 4 will be from 1 to 2 mm, preferably 1 mm.

In the case of FIG. 2 where the tube is an insert in the cast piece, these plays are obtained by coating the ends of the tube 10 with a thick paste.

The arrangements of the openings of FIGS. 3 and 4, a and b, permit, with the blocking by a weld on one side of tube 11, against rotation in the seat in the sleeve, while leaving the other side of the tube free to expand (with the plays provided), the rotation of the zirconia tube 7 by a half turn after a certain number of kilometers and the presentation before the holes in tube 11 of a catalytic coating, still free of erosion, to prolong, for an equal number of kilometers, the operating lifetime of the electrolyte tube 7.

The electrical contacts between the surface electrodes of the tube 7 will consist, for the negative pole, of a contact with the external catalytic coating by the intermediary of the copper-graphite seal 5, the contact being obtained quite naturally by the pressure of the seal against the surface.

The connection to the positive pole is effected by the soldering of a contact wire 14 to the inner coating of the zirconia tube 7, the wire being brought out through the insulating piece 13.

In the cases of FIGS. 5 and 6, the negative pole consists of a contact with the external catalytic coating by the intermediary of a pre-formed seal 21, e.g. of stainless steel wool, kept compressed by the insulating pieces 19 and 28.

The positive pole will be realized by the same method as in the cases of FIGS. 1 and 2, by soldering the wire 14 to the internal metallized surface of the tube 7. One could also use the tubular shape to good effect, realizing the electrical contact to the inner surface by a spring-metal means compressed against the inner wall of the tube and connected to the wire 14. This solution has the advantage of rendering the electrolyte tube easily interchangeable.

The negative pole constituted by the external face of the electrolyte tube 7 and its catalytic coating is in electrical contact with seal 5, which itself is in electrical contact with tubular body 4 connected to the body of the vehicle.

A similar electrical connection holds for the embodiment of FIG. 6. An electrical contact is established between the external surfaces of electrolyte tube 7 and plug 26 by electrically contacting pre-formed seal 21. Thus, the negative electrical connection is effected by soldering a wire to the outside of tubular body 4 or plug 26, anywhere on the body of the vehicle.

The metallization of the electrolyte tube 7 will be realized to advantage over its entire outer surface in contact with the gas being measured by a coating of metal in divided state obtained by projection or vaporization in a vacuum, the metal having a catalytic effect on the gas measured.

For example, in an application of monitoring the composition of the exhaust gas of a motor, this catalytic effect will be able to act on the combination of the carbon monoxide and hydrogen of the combustion gases with the excess oxygen in the region of the surface of the electrolyte tube 7, thus permitting increased sensitivity in the measurement of the excess or deficiency of oxygen in the gaseous mixture with respect to the stoichiometric proportions of the combustion products.

Figure 7:
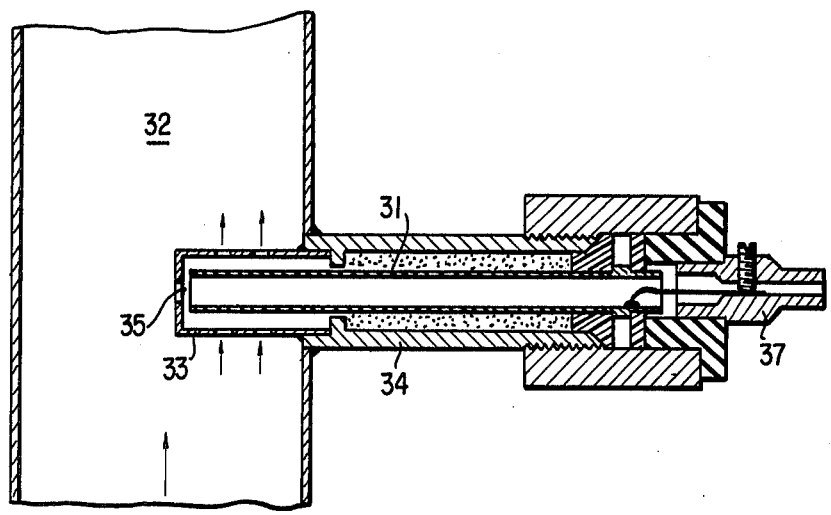
FIGS. 7 and 8 show two examples of the same preferred embodiments.

In FIG. 7 a sleeve 34 is welded to a pipe 32 conducting the gases to be measured, e.g., the exhaust gases of an internal combustion engine, the sleeve being threaded at the end and containing a system of stuff joint and seal clamping one end of the electrolyte tube 31. The sleeve 34 may possibly have cooling fins (not shown).

According to the invention, the tube 31 and its surrounding tube 33 for protection in the gas conduit 32 project into this conduit transverse to the flow with their free end 35 opening into the said conduit. This end opens, to advantage, in the central region of the conduit 32 and the tube 33 is partially closed over the end of the tube 31 partly covering the opening in the latter. The tube 33 has perforations 36 as indicated previously. At the other end of the tube 31, the piece 37 for electrical communication with the inner surface of the tube is tubular in shape, permitting a introduction of the reference air flow. This air may be supplied from a pressurized source, such as an air pump, being maintained at a slightly higher pressure than the exhaust gases.

Figure 8:
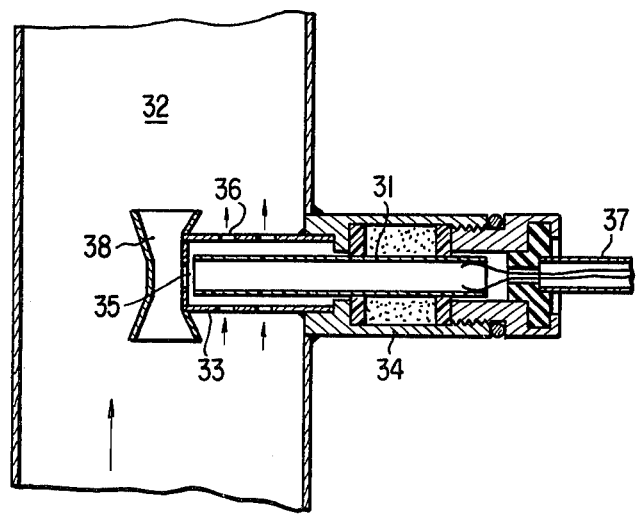

This pressurized supply may be combined with or replaced by an aspiration of the air into the exhaust pipe induced by the flow of the analyzed gases in the passage 32 near orifice 35. The aspiration effect may be enhanced by placing a venturi 38 at the end of tube 33, as shown in FIG. 8.

More generally stated, while its outer surface is bathed by the flow of gases to be measured, the electrolyte tube 31 projects transversely in the flow passage 32 releasing its reference gas into the passage through the orifice 35 in the end of the tube.

A tube 33 with multiple perforations 36 also mounted transversely in the passage 32 encloses, without contacting, the electrolyte tube 31, partially covering the end of tube 31 where the reference gas is released. At the end of the electrolyte tube 31 outside the conduit 32, the piece 37 providing electrical communication with the inner surface of the tube has a tubular form, permitting the introduction of the reference gas flow. The reference gas flows through the interior of the electrolyte tube at a pressure slightly greater than that of the gas to be measured flowing in the passage 32.

The free end 35 of the tubes 33 and 31 opens essentially into the center of the flow passage 32 of the gas to be tested.

The aspiration effect may be intensified by a venturi 38 mounted at the end of the protective tube 33, the outlet orifice 35 for the reference gas opening into the throat of the venturi.

Obviously many modifications and variations of the present invention are possible in light of the above teachings. It is therefore to be understood that within the scope of the appended claims, the invention may be practiced otherwise than as specifically described herein.

I claim:

1. A probe system for detecting variations in the composition of a flow of mixed gases to be measured on the pile effect in a solid electrolyte, one side of which is subjected to the mixed gases to be measured and the other side to a reference gas, which comprises:
   a conduit through which the mixed gases to be measured flow;
   a solid electrolyte comprising a tube open at its ends;
   means for passing the reference gas through the interior of said tube wherein said tube is mounted transversely in said conduit and,
   at least one seal interconnecting said tube and said conduit.

2. A detecting probe system as set forth in claim 1, wherein: walls of the conduit receive axially aligned tubular bodies in which are compressed said at least one seal, providing the centering of and maintaining the axial position of said electrolyte tube passing through said at least one seal.

3. A detecting probe system as set forth in claim 2, further comprising threaded plugs, bored out with a central hole, into which the ends of the electrolyte tube fit without contact and with clearance at the end, for compressing said seals.

4. A detecting probe system as set forth in claim 3, further comprising a connecting wire, led in through the central hole in an insulating plug for the introduction of the reference gas, for making electrical contact with the inner surface of said electrolyte tube.

5. A detecting probe system as set forth in claim 4, wherein the electrical contact of said connecting wire against the inner surface of said electrolyte tube is provided by the compression of a spring-metal clip.

6. A detecting probe system as set forth in claim 2, wherein said seals are formed as sleeves of copper-graphite compressed between pairs of washers of refractory metal alloy felt making electrical contact with the outer surface of said electrolyte tube.

7. A detecting probe as set forth in claim 2, wherein said tubular bodies have an elongated form, assuring cooling of their ends against the heating by the flow of gas to be measured.

8. A detecting probe system as set forth in claim 7, wherein seals compress a longitudinal seal of thermo-expandable material filling the space between said tubes of elongated form and said electrolyte tube.

9. A detecting probe as set forth in claim 1, further comprising a protective tube surrounding, without contacting, said electrolyte tube and having perforations which provide passage for said mixed gases around the outer surfaces of said electrolyte tube.

10. A detecting probe system as set forth in claim 9, wherein said perforations consist of at least one longitudinal slot in the frontal zone of said protective tube receiving the flow of gas to be measured and lateral perforations for the escape of the flow entering the frontal slot.

11. A detecting probe system as set forth in claim 9, wherein said perforations consist of two lines of orifices diametrically opposed in the direction of flow of the gases to be measured.

12. A detecting probe as set forth in claim 9, wherein said tubular bodies receiving said seals are made in a single casting of refractory iron.

13. A detecting probe system as set forth in claim 12, wherein said protective tube is introduced into said casting as an insert, its ends being kept free by first coating them with a thick paste.

14. A detecting probe system as set forth in claim 1, wherein said electrolyte tube receives over its entire outer surface in contact with the gases to be measured, a coating of finely divided metal, serving as the electrolyte pile electrode, while also providing a catalytic effect in the combination of carbon monoxide CO and hydrogen $H_2$ with oxygen $O_2$, this in a small volume around the electrolyte tube in the case of a flow of mixed gases consisting of the exhaust gases of a motor.

15. A detecting probe system as set forth in claim 1, wherein:
    said tube is transversely mounted on a diametric axis of said conduit.

16. A probe system for detecting variations in composition of a flow of mixed gases to be measured based on a pile effect in a solid electrolyte, one side of which is exposed to the mixed gases to be measured and the other side to a reference gas, including a conduit and wherein the solid electrolyte comprises a tube open at its ends and means for circulating the reference gas in the interior of said tube, the outer surface of which is bathed by the flow of said mixed gases in the conduit to be measured, said electrolyte tube being transversely mounted in said conduit and projecting into the conduit of said mixed gases and the reference gas being released into said conduit through an orifice in the end of said tube.

17. A detecting probe system as set forth in claim 16, further comprising a tube with multiple perforations, also mounted transversely in said conduit, surrounding, without contacting, said electrolyte tube, its end partially enclosing the end of said electrolyte tube from which the reference gas is released.

18. A detecting probe system as set forth in claim 17, wherein at the end of said electrolyte tube outside said conduit, a piece is disposed providing electrical communication with the inner surface of the tube having a tubular form, permitting the introduction of the flow of reference gas.

19. A detecting probe as set forth in claim 16, wherein a venturi is mounted on the end of said tube with multiple perforations and into the throat of which said orifice for the flow of reference gas opens.

20. A detecting probe system as set forth in claim 16, wherein:
    said tube is transversely mounted on a diametric axis of said conduit.

* * * * *